US010139412B2

(12) United States Patent
Vadasz et al.

(10) Patent No.: US 10,139,412 B2
(45) Date of Patent: Nov. 27, 2018

(54) SEMAPHORIN 3A AS A DIAGNOSTIC MARKER FOR UROTHELIAL CANCER

(71) Applicants: THE FUND FOR MEDICAL RESEARCH, DEVELOPMENT OF INFRASTRUCTURE AND HEALTH SERVICES—BNAI ZION MEDICAL CENTER, Haifa (IL); TECHNION RESEARCH & DEVELOPMENT FOUNDATION LIMITED, Haifa (IL)

(72) Inventors: Zahava Vadasz, Haifa (IL); Sarel Halachmi, Haifa (IL); Jacob Rubinstein, Haifa (IL); Ofer Nativ, Haifa (IL); Elias Toubi, Haifa (IL)

(73) Assignees: The Fund for Medical Research, Development of Infrastructure and Health Services—Bnai Zion Medical Center, Haifa (IL); Technion Research and Development Foundation Limited, Haifa (IL)

(*) Notice: Subject to any disclaimer, the term of this patent is extended or adjusted under 35 U.S.C. 154(b) by 0 days.

(21) Appl. No.: 15/101,112

(22) PCT Filed: Dec. 2, 2014

(86) PCT No.: PCT/IL2014/051043
§ 371 (c)(1),
(2) Date: Jun. 2, 2016

(87) PCT Pub. No.: WO2015/083156
PCT Pub. Date: Jun. 11, 2015

(65) Prior Publication Data
US 2016/0299142 A1    Oct. 13, 2016

Related U.S. Application Data

(60) Provisional application No. 61/910,441, filed on Dec. 2, 2013.

(51) Int. Cl.
*G01N 33/53*    (2006.01)
*G01N 33/574*   (2006.01)

(52) U.S. Cl.
CPC . *G01N 33/57407* (2013.01); *G01N 33/57434* (2013.01); *G01N 33/57438* (2013.01); *G01N 33/57484* (2013.01); *G01N 2333/4703* (2013.01); *G01N 2333/4704* (2013.01); *G01N 2800/52* (2013.01)

(58) Field of Classification Search
None
See application file for complete search history.

(56) References Cited

U.S. PATENT DOCUMENTS

2013/0184172 A1    7/2013 Goodison et al.

OTHER PUBLICATIONS

Yacoub et al (Histopathology, 2009, 55: 392-398).*
Tockman et al (Cancer Res., 1992, 52:2711s-2718s).*
Muller, Michael W. et al., "Associateion of axon guidance factor semaphorin 3A with poor outcome in pancreatic cancer" Int. J. Cancer (2007) vol. 121, pp. 2421-2433.
Zhou, Haiying et al., "Significance of semaphorin-3A and MMP-14 protein expression in non-small cell lung cancer" Oncology Letters (2014) vol. 7, pp. 1395-1400.
Bagci, T. et al. "Autocrine semaphorin 3A signaling promotes glioblastoma dispersal" Oncogene (2009) vol. 28, pp. 3537-3550.
Neufeld, Gera et al., "Semaphorins in Angiogenesis and tumor progression" Cold Spring Harb Perspec Med (2012), pp. 1-13.
Vadasz, Zahava et al., "Semaphorin 3A is a marker for disease activity and a potential immunoregulator in systemic lupus erythematosus" Arthritis Research & Therapy (2012) vol. 14, pp. 1-8.
Catalano, Alfonso et al., "Semaphorin-3A is expressed by tumor cells and alters T-cell signal transduction and function" Blood (2006) vol. 107(8), pp. 3321-3329.
Lepelletier, Yves et al., "Immunosuppressive role of semaphorin-3A on T cell proliferation is mediated by inhibition of actin cytoskeleton reorganization" Eur. J. Immunol. (2006) vol. 36, pp. 1782-1793.
Vadasz, Zahava et al., "The involvement of immune semaphorins and neuropilin-1 in lupus nephritis" Lupus (2011) vol. 20, pp. 1466-1473.
Ji, Jong-Dae et al., "Expression and function of semaphorin 3A and its receptors in human monocyte-derived macrophages" Human Immunology (2009) vol. 70, pp. 211-217.
Written Opinion of the International Searching Authority for PCT/IL2014/051043 dated Mar. 6, 2015, pp. 1-4.
The International Search Report for PCT/IL2014/051043 dated Mar. 6, 2015, pp. 1-4.

* cited by examiner

*Primary Examiner* — Sean E Aeder
(74) *Attorney, Agent, or Firm* — McDonnell Boehnen Hulbert & Berghoff LLP (57) ABSTRACT

The present invention is directed to methods and kits useful for diagnosis and/or prognosis of urothelial cancer in a subject. The present invention further relates to methods of assessing severity of cancer and methods of determining efficacy of a treatment for cancer. The methods and kits of the invention comprise determining the levels of semaphorin 3A in a biological sample of a subject.

10 Claims, 5 Drawing Sheets

SEMAPHORIN 3A AS A DIAGNOSTIC MARKER FOR UROTHELIAL CANCER

CROSS-REFERENCE TO RELATED APPLICATIONS

This application is a U.S. national phase of International Application No. PCT/IL2014/051043, filed on Dec. 2, 2014, which claims priority to U.S. Provisional Application No. 61/910,441, filed Dec. 2, 2013, both of which are incorporated by reference herein in their entirety.

FIELD OF THE INVENTION

The present invention is directed to methods and kits useful for diagnosis and/or prognosis of urothelial cancer in a subject. The present invention further relates to methods of assessing severity of cancer and methods of determining efficacy of a treatment for cancer. The methods and kits of the invention comprise determining the levels of semaphorin 3A in a biological sample of a subject.

BACKGROUND OF THE INVENTION

Semaphorins

Semaphorins are a family of membrane bound and secreted proteins classified into eight sub-classes based on their structural domains. Semaphorins mainly regulate focal adhesion assembly/disassembly and induce cytoskeletal remodeling, thus affecting cell shape, cell attachment to the extracellular matrix, cell motility, and cell migration. Although Semaphorins were originally identified as affecting axon guidance during development of the nervous system, they are now thought to fulfill diverse physiological roles including organogenesis, vascularization, angiogenesis, neuronal apoptosis, and neoplastic transformation. Additionally, recent studies pointed to the involvement of Neuropilin-1 (a receptor for semaphorin 3) and certain Semaphorins in the regulation of the immune system, and thus these Semaphorins are denoted "immune Semaphorins".

The seven class-3 Semaphorins (Semaphorin 3s), designated by the letters A-G, are the only vertebrate secreted Semaphorins. Neuropilins (Nrps) and the type A/D family Plexins (Plexin-A1, -A2, and -A3, and Plexin-D1) act as receptors for Semaphorin 3. Each Semaphorin 3 family member shows distinct binding preference for Nrps. Each Sema3-Nrp complex associates with specific plexins to mediate downstream signaling. Most membrane-bound vertebrate Semaphorins directly bind plexins, while class-3 Semaphorins require Neuropilins as obligate co-receptors.

Semaphorin 3A (hereinafter "Sema3A"), a class-3 secreted member of the Semaphorin family, has been established as an axonal guidance factor during development. Interestingly, several lines of evidence suggest that Sema3A also affects immune cell functions. Sema3A has been shown to be expressed by activated T cells and inhibit T cell proliferation and cytokine secretion (Catalano, A. et al., 2006, Blood 107: 3321-3329; Lepelletier, Y. et al., 2006, Eur. J. Immunol. 36: 1782-1793). Moreover, the expression of Sema3A, Neuropilin 1 (NP-1), Neuropilin 2 (NP-2), and Plexins was found to be increased on differentiating macrophages and on activated T cells (Ji J D et al., 2009, Human Immunol., 70(4): 211-7). In another study, kidney biopsies from lupus glomerulonephritis (LGN) patients showed stronger staining with anti-NP-1, anti-Semaphorin 3A and anti-Semaphorin 4A antibodies as compared with either normal biopsies or biopsies from patients with primary nephropathy and proteinuria (Vadasz Z. et al., 2011, Lupus, 20:1466-1473). A subsequent study has shown that Sema3A serum levels in SLE patients are significantly lower than in healthy individuals (Vadasz Z. et al., 2012, Arthritis Research & Therapy, 14:R146).

Semaphorins in Cancer

Semaphorin 3A was found to be related to several malignancies. In breast cancer semaphorin impedes tumor cell migration and growth (Mishra R. et al., Oncogene 2014, 1-12). Glioblastoma Multiforma, is a malignant type of glioma having a tendency for aggressive local spread. This tumor expresses high level of semaphorin 3A receptor (T. Bagci et al., Oncogene (2009) 28, 3537-3550). Lower expression of semaphorin-3A was detected in Non Small Cell Lung Cancer (NSCLC) tissues following comparison with control non cancerous lung tissues (Zhou H. et al., Oncology Letters 7: 1395-1400, February 2014).

Urothelial Cell Carcinoma

Urothelial Cell Carcinoma (UCC), also known as Transitional Cell Carcinoma (TCC), is a type of cancer that typically occurs in the urinary collecting system (the kidney, ureters, urinary bladder, urethra and accessory organs). It is the most common type of bladder cancer and cancer of the ureter, urethra, renal pelvis and calices and also urachus. It is the second most common type of kidney cancer, but accounts for five to 10 percent of all primary renal malignant tumors and over 90% of bladder tumors. TCC arises from the transitional epithelium, a tissue lining the inner surface of these hollow organs. Patients with non invasive urothelial carcinoma are at a high risk for recurrence and progression, therefore a lifelong follow-up is needed.

Bladder cancer is the fourth most common cancer in the United States. The disease exists in two main forms: non-invasive bladder carcinoma, which lacks invasion into surrounding muscle tissue and is the more common form accounting for 75% of all cases, and muscle invasive bladder carcinoma, in which the tumor spreads through the lining of the bladder and invades the muscular wall of the bladder. Invasive cancer may grow through the bladder wall and spread to nearby organs. The muscle invasive tumors are associated with a high risk of metastases and a poor prognosis.

The gold standard for detecting bladder cancer is cystoscopy (an endoscopy of the urinary bladder in which a fiber optic device is inserted via the urethra). However, this procedure is invasive, uncomfortable, costly and may provoke bleeding, infection, urethral trauma, and urethral stricture. Moreover, cystoscopy may miss certain lesions, in particular small areas of carcinoma in situ. Computed Tomography (CT) scans may also be utilized for diagnosis of bladder cancer but this procedure exposes the patient to an ionizing radiation, and thus may lead to secondary malignancy. CT scans are further associated with intravenous contrast material injection which may cause anaphylactic shock, renal failure and cardio-vascular failure. Urine cytology, which assesses presence of cancerous cells in the urine, is the only noninvasive method used to detect recurrent bladder cancer, however it has a sensitivity of 50% at best.

There remains an unmet need for reliable, and accurate non invasive methods for diagnosing urothelial cancer in a subject and for determining disease staging and prognosis. There is also an unmet need of methods for determining the effectiveness of an anti-cancer therapy of a subject. A sensitive and specific method for disease detection would allow screening population at risk and healthy population. This cannot be done today as cytology sensitivity is low.

SUMMARY OF THE INVENTION

The present invention provides methods and kits for the diagnosis, prognosis and monitoring progression of urothelial cancer in a subject. The methods comprise determining the level of semaphorin 3A in a biological sample of a subject and comparing those levels to a reference or control sample. Advantageously, the invention provides simple, reliable, highly sensitive and cost effective methods for determining the presence of urothelial cancer in a subject. The invention further provides methods and kits for determining efficacy of a treatment for cancer.

As exemplified hereinbelow, detection of semaphorin 3A in a urine sample positively correlates with the presence of bladder tumor in a subject. Moreover, higher tumor size and progressive tumor stage correlate with higher levels of semaphorin 3A in the urine sample.

The present invention, in some embodiments thereof discloses, for the first time, the use of semaphorin 3A as a biomarker for bladder cancer detection, prognosis and treatment follow-up.

According to one aspect, the present invention provides a method for diagnosing urothelial cancer in a subject, comprising determining the levels of semaphorin 3A or a derivative thereof, in a biological sample obtained from the subject, wherein an elevation in the levels of the Semaphorin 3A compared to a control value is indicative of urothelial cancer in said subject. According to some embodiments, the urothelial cancer is bladder cancer. According to additional embodiments, the bladder cancer is transitional cell carcinoma.

According to another embodiment, the biological sample is a fluid sample. According to yet another embodiment, the biological sample is a solid sample. According to yet another embodiment, the fluid sample is selected from the group consisting of: urine, whole blood, plasma, serum, and ascitic fluid. According to yet another embodiment, the fluid sample is a urine sample. According to some embodiments, the biological sample is obtained by non-invasive means.

According to some embodiments, the biological sample is fluid and the method further comprises filtering the fluid sample. According to some embodiments, the biological sample is urine and the method further comprises filtering the urine sample. According to yet another embodiment, the fluid sample is urine and is free of residual cells. According to further embodiments the sample is urine and the sample is concentrated prior to analysis. According to yet another embodiment, the method of the invention is useful for determining at least one of: presence of cancer, cancer recurrence, stage of cancer and efficacy of a cancer treatment.

According to yet another embodiment, the control value is selected from the group consisting of: a predetermined cutoff value, a value obtained from a healthy individual, a panel of values from a set of healthy individuals and a value or a set of values obtained from a group of individuals afflicted with defined severities of cancer. According to yet another embodiment, the predetermined cutoff value is obtained from said subject at at-least one prior-referenced time point.

According to yet another embodiment, determining the levels of semaphorin 3A comprises determining the protein, polypeptide or peptide levels of semaphorin 3A. Each possibility represents a separate embodiment of the invention.

According to yet another embodiment, determining the levels of semaphorin 3A is performed by an immunoassay. According to yet another embodiment, the immunoassay comprises contacting the biological sample with an antibody directed to semaphorin 3A. According to yet another embodiment, the method further comprising determining the presence of semaphorin 3A-antibody complex formed. According to yet another embodiment, the method further comprising quantifying the amount of semaphorin3A-antibody complex formed.

According to yet another embodiment, the method further comprising administering a treatment for bladder cancer to a patient diagnosed as having bladder cancer.

According to yet another embodiment, the method of the invention is qualitative, quantitative or both.

According to another aspect, the invention provides a method for determining efficacy of a treatment for a bladder cancer in a subject in need thereof, said method comprising:
 a) determining the levels of Semaphorin 3A in a first biological sample of said subject;
 b) treating said subject with an anticancer treatment;
 c) determining the levels of Semaphorin 3A in a second biological sample of said subject; and
 d) comparing the levels of Semaphorin 3A in said first and second biological samples,
 wherein a decrease in Semaphorin 3A levels from the first to the second biological sample is indicative of said treatment being efficacious.

According to one embodiment, step a) is conducted at a time point prior to or during step b). According to another embodiment, steps a) and c) are conducted at distinct time points during step b).

According to yet another aspect, the present invention provides a kit for the prognosis, diagnosis, monitoring cancer severity or determining efficacy of a treatment for cancer, comprising means for determining the levels of semaphorin 3A, or a derivative thereof, in a biological sample of a subject and instructions for using said kit in the diagnosis, prognosis, monitoring cancer severity or determining efficacy of a treatment for cancer.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

According to some aspects, the present invention provides methods and kits for diagnosing urothelial cancer, particularly of the bladder in a subject, wherein semaphorin 3A, or a derivative thereof is used as a biomarker. The methods of the invention are also useful for determining the severity of the cancer. Further, the methods are useful for determining the effectiveness of a treatment for cancer.

The present invention discloses for the first time the unexpected discovery that the detection of Semaphorin 3A in a urine sample obtained from a subject reflects the presence of bladder cancer in the tested subject. The non invasive method used today for assessing bladder cancer is cytology, but it commonly provides false negative results. Hence, the use of semaphorin 3A as a biomarker of cancer overcomes the drawbacks of currently used diagnostic methods in providing a more sensitive, reliable, simple and cost effective method for detecting bladder cancer.

Thus, the present invention provides methods and compositions for assessing the presence of urothelial cancer. The present invention further provides methods and compositions for determining severity or stage of the cancer disease. According to further embodiments, the present invention provides methods and compositions for determining the effectiveness of a treatment for cancer.

According to certain embodiments, the present invention provides methods and kits useful for diagnosis of urothelial cancer based on the levels of semaphorin 3A in a sample obtained from a subject.

As used herein the term "urothelial cancer" refers to an abnormal and/or malignant growth of the urothelium. When the term "urothelial cancer" is used, it specifically refers to a carcinoma of the urothelium, meaning a transitional cell carcinoma (TCC) of the urinary system. The urothelium is a layer of tissue that lines the urethra, bladder, ureters, prostate, and renal pelvis. The present invention encompasses all the aforementioned types of cancers of the urothelium. Thus, according to some embodiments, the cancer is a urothelial cancer, which affects a urothelial tissue selected from the group consisting of: bladder, urethra, ureters, prostate, and renal pelvis. Each possibility represents a separate embodiment of the invention.

The methods of the invention are of particular relevance to tumors of the bladder. Bladder cancer is classified as one of the cancers of the urinary tract. Ninety percent of bladder cancer cases are Transitional Cell Carcinomas (TCC) that arise from the inner lining of the bladder called the urothelium. The urothelium is a layer of tissue that lines the urethra, bladder, ureters, prostate, and renal pelvis. The other 10% of tumors are squamous cell carcinoma, adenocarcinoma, sarcoma, small cell carcinoma and secondary deposits from cancers elsewhere in the body.

According to some embodiments, the invention provides means which specifically and accurately discriminate between patients afflicted with urothelial cancer and healthy control subjects. According to some embodiments, the invention provides means which discriminate between patients afflicted with urothelial cancer and patients afflicted with non-malignant conditions. Non-malignant conditions may be for example, conditions accompanied by hematuria, which present blood components in the urine. According to some embodiments, the invention provides means for assessing the cancer stage. According to some embodiments, the methods of the invention are useful for discriminating between non-invasive and invasive bladder cancer.

It is to be understood that Semaphorin 3A is interchangeable with any alternative name or synonym of this protein known in the art. Typical semaphorin 3A synonyms include, but are not limited to, collapsin 1, semaphorin III and Sema 3A.

As used herein the term "derivative thereof" may also be referred to as an analogue. The term encompasses any form of naturally occurring semaphorin 3A and include splice variants of semaphorin 3A, or mutant forms of semaphorin 3A. Mutant forms of semaphorin 3A include truncated, or point mutated forms of semaphorin 3A.

As used herein the terms "diagnosing" or "diagnosis" refer to the process of identifying/detecting cancer in a subject. Furthermore, the term encompasses screening for a cancer, determining the grade of the cancer, determining the stage of the cancer, distinguishing a cancer from other cancers including those cancers that may feature one or more similar or identical symptoms, providing prognosis of a cancer, monitoring cancer progression or relapse, assessing treatment efficacy, selecting a therapy for a cancer, optimization of a given therapy for a cancer, monitoring the treatment of a cancer, and/or predicting the suitability of a therapy for specific patients or subpopulations or determining the appropriate dosing of a therapeutic product in patients or subpopulations.

According to some embodiments, the methods of the invention encompass diagnosing bladder cancer in a symptomatic subject. According to other embodiments, the methods of the invention encompass diagnosing bladder cancer in an asymptomatic subject. An asymptomatic subject may be, for example, evaluated for monitoring recurrence of cancer.

The method of diagnosing cancer of the present invention may encompass, apart for the determining the levels of semaphorin 3A, any known methodologies used to diagnose a urothelial cancer.

As used herein the term "determining the levels of semaphorin 3A" encompasses determining the levels of an mRNA or a peptide, a polypeptide or a protein of Semaphorin 3A.

According to some embodiments, the levels of semaphorin 3A are the expression levels of the Semaphorin 3A protein. According to some embodiments, the levels of semaphorin 3A are the expression levels of the Semaphorin 3A transcript (mRNA). According to some embodiments, the level of semaphorin 3A is the concentration of a secreted form of this protein in a bodily fluid sample (e.g. a urine sample).

According to some embodiments, "determining the levels of semaphorin 3A" may be performed by any method known in the art. These may include, but are not limited to, immunoassays, analytic biochemical methods, amplification methods, hybridization methods, methods utilizing a biosensor device and the alike. Each possibility represents a separate embodiment of the invention.

An immunoassay is characterized by the use of specific binding properties of a particular antibody to an antigen target (e.g., the biomarker of the invention) and/or quantifying the complex antibody-antigen formed. For example, an antibody may be synthesized or commercially purchased to detect semaphorin 3A specifically. Thus, the immune reactivity of the antibody to the antigen, i.e. its ability to specifically bind the antigen, may be used to determine the amount of the antigen in the sample.

According to some embodiments, immunoassays include, but are not limited to, enzyme-linked immunosorbant assay (ELISA), gel precipitation reactions, immunodiffusion (single or double), immunohistochemistry, immunoelectrophoresis, radioimmunoassay (RIA), immunofluorescent assay, Western blotting, Fluorescence Activated Cell Sorter (FACS), an antibody microarray chip, a bead flow cytometry and the like. Each possibility represents a separate embodiment of the invention.

According to one embodiment, the detection of the biomarker is performed using an ELISA testing kit. In such assay, samples are typically incubated in the presence of an immobilized first specific binding agent (e.g. an antibody) capable of specifically binding the biomarker. Binding of the biomarker to said first specific binding agent may be measured using any one of a variety of known methods, such as using a labeled second specific binding agent capable of specifically binding the biomarker (at a different epitope) or the first specific binding agent.

According to some embodiments, analytic biochemical methods include, but are not limited to, electrophoresis, capillary electrophoresis, high performance liquid chromatography (HPLC), thin layer chromatography (TLC), affinity chromatography, hyperdiffusion chromatography, mass spectroscopy and the like. Each possibility represents a separate embodiment of the invention.

According to some embodiments, amplification methods include polymerase chain reaction (PCR). PCR may either be quantitative real-time PCR (qRT-PCR) or reverse transcription PCR (RT-PCR). Each possibility represents a separate embodiment of the invention.

According to some embodiments, hybridization methods, include, but are not limited to Northern blotting, in situ hybridization, and fluorescent in situ hybridization (FISH). Each possibility represents a separate embodiment of the invention.

According to some embodiments, the "levels of semaphorin 3A" may be determined by quantitative as well as qualitative measurement. Each possibility represents a separate embodiment of the invention.

According to some embodiments, the phrase "qualitative" refers to differences in the levels of a biomarker, and denotes the presence versus absence of Semaphorin 3A levels/expression. According to some embodiments, the phrase "quantitative" refers to differences in the levels of a biomarker and denotes absolute differences in quantity of expression, as determined by any means, known in the art. According to some embodiments, "quantitative" refers to relative differences, which may be statistically significant, or in some embodiments, when viewed as a whole or over a prolonged period of time, etc., indicate a trend in terms of differences in Semaphorin 3A levels.

As used herein the term "elevation" of semaphorin 3A refers, according to some embodiments, to a statistically significant elevation, or in other embodiments to a significant elevation as recognized by a skilled artisan. The term is interchangeable with an increase. According to some embodiments, level is amount. According to some embodiments, levels of semaphorin 3A reflect the expression of this protein, peptide, polypeptide or mRNA in a biological sample of a subject. According to some embodiments, levels of semaphorin 3A reflect the secretion of this protein, peptide, polypeptide from within cells and presence in a biological sample.

According to some embodiments, a statistically significant difference between the level of semaphorin 3A in the sample obtained from the subject compared to a normal level of semaphorin 3A (e.g., the level in a healthy control population) is an indication that the subject is afflicted with urothelial cancer (for example, bladder cancer). According to other embodiments, a statistically significant difference between the level of the semaphorin 3A in the sample obtained from the subject compared to the level of semaphorin 3A in a subject afflicted with non-invasive cancer (e.g., the level in a control population of non-muscle invasive bladder cancer patients) is an indication that the subject is afflicted with an invasive bladder cancer.

According to some embodiments, "an elevation" of semaphorin 3A" refers to higher levels of Semaphorin 3A or an increase in the levels of Semaphorin 3A in the tested biological sample as compared to the control sample/value. According to some embodiments, "an elevation of Semaphorin 3A" may be an elevation by at least 1.2, 1.4, 1.6, 1.8, 2, 3, 4, or 5 fold as compared to the control value. Each possibility represents a separate embodiment of the present invention.

According to some embodiments, "an elevation of Semaphorin 3A" may be an elevation by at least 10%, at least 20%, at least 30%, at least 40%, at least 50%, at least 60%, at least 70% or at least 80% of the tested biological sample as compared to the control value. Each possibility represents a separate embodiment of the present invention.

As used herein the term "control value" denotes a reference value or range of plurality of values indicative of a healthy state or of a specific stage of the urothelial cancer (degree of severity of the disease). According to some embodiments, a control value may represent an average value of semaphorin 3A calculated from a group of healthy subjects or of subjects afflicted with a specific stage of the urothelial cancer. The control value may be a predetermined cutoff/threshold value obtained from the subject being diagnosed of cancer at at-least one prior-referenced time point. In some embodiments, the control value is zero (i.e., non detectable level). The manner of selecting the number of subjects used for a defining a group should be known to those skilled in statistical analyses. Further, the value may be a reference point determined based on the level of semaphorin 3A in a sample taken from the examined subject at at-least one earlier time point, for example when the subject was first diagnosed as having cancer or at a later time point. The level at that time point being the reference point for any follow up diagnosis of the subject's state making use of the method of the present invention.

As used herein the term "biological sample" refers to any sample obtained from the subject being tested. According to some embodiments, the biological sample is a biopsy. According to some embodiments, the biological sample is selected from: cells, tissue and bodily fluid. Each possibility represents a separate embodiment of the invention. According to some embodiments, the biological sample is a solid or a tissue sample. According to some embodiments, the biological sample is a fluid sample. According to some embodiments, the fluid sample is selected from the group consisting of: urine, whole blood, plasma, serum, and ascitic fluid. Each possibility represents a separate embodiment of the invention. According to one embodiment, the fluid sample is a urine sample. According to some embodiments, the solid sample or tissue sample is obtained from the tumor. According to some embodiments, the biological tissue sample is obtained from a urothelial cancer of a tissue selected from the group consisting of: bladder, urethra, ureters, prostate, and renal pelvis. Each possibility represents a separate embodiment of the invention.

The biological sample is obtained or collected from the subject in any method known in the art. The sample may be collected from the subject by noninvasive, invasive or minimal invasive means. Each possibility represents a separate embodiment of the invention.

According to some embodiments, the sample is obtained from the bladder. According to some embodiments, the sample is obtained from the bladder without a preceding step of bladder scraping or washing. According to some embodiments, the sample is a fluid (e.g., a urine sample) and there is no need to isolate or enrich exfoliated tumor cells in the sample prior to detection. According to some embodiments, the sample is a non-sedimented urine sample.

According to some embodiments, the sample may be treated prior to being subjected to the methods of the present invention. According to some embodiments, the sample is a fluid sample and is substantially free of residual cells or debris of cells. For removing cells or debris of cells from within a bodily fluid sample, said cells or debris of cells may be precipitated by centrifugation and the supernatant is taken for determining the semaphorin 3A levels. Typically, centrifugation of up to 2500 revolutions per minute (rpm) for up to 20 min is performed. A common centrifugation procedure is associated with centrifugation of 1100 rpm for 7 min, or centrifugation of 2000 rpm for 5 min. Alternatively, cells can be removed by filtration. According to some embodiments, the liquid sample undergoes concentration with a suitable membrane pore cut-off size. According to various embodiments, a filter with a membrane cut-off of: 5,000, 10,000, 30,000 or 50,000 kDa is used. Each possibility represents a separate embodiment of the present invention. In accordance with this embodiment, a fluid sample treated with such filter is concentrated, namely, any molecule, particle below the size of the cut-off of the filter is removed. According to some embodiments, the liquid sample is concentrated by up to 100 times the initial concentration. According to a particular embodiment, the liquid sample is concentrated by up to 50 times the initial concentration. According to another embodiment, the liquid sample is diluted 1:10 for instance, using PBS. According to another embodiment, the sample is diluted 1:4, 1:6, 1:8, 1:10, 1:15 or 1:20. Each possibility represents a separate embodiment of the present invention.

According to some embodiments, the sample is a fluid sample and the cells within said fluid sample are analysed. In accordance with some embodiments, the sample is centrifuged, the supernatant is removed and the cells are analysed for semaphorin 3A levels of expression. According to some embodiments, the sample is reconstituted (e.g. with fluids, such as, PBS or cell media). According to alternative embodiments the fluid sample is analyzed together with the cells present therein without prior separation.

According to additional embodiments, the sample may conveniently be frozen after being collected from the subject and thawed before determining the levels of semaphorin 3A, e.g. by an immunoassay.

According to some embodiments, the sample is selected from the group consisting of formalin-fixed paraffin-embedded (FFPE) tissue, fresh frozen (FF) tissue, and tissue comprised in a solution that preserves nucleic acid or protein molecules. Each possibility represents a separate embodiment of the invention.

It should be noted that a "biological sample obtained from the subject" may also optionally comprise a sample that has not been physically removed from the subject.

According to some embodiments, there are provided methods for the detection of cancer condition in a subject, the methods comprise detecting or determining Semaphorin 3A level in a biological sample of the subject, wherein an elevation in the levels of the Semaphorin 3A compared to a control value is indicative of cancer in said subject. In some embodiments, the control value is zero (i.e., non detectable level). In some embodiments, the control value is any predetermined value. In some embodiments, the methods are qualitative. In some embodiments, the methods are quantitative. In some embodiments, the biological sample is obtained from the subject by non-invasive means.

According to some embodiments, the methods for detection of cancer condition a subject comprise the steps of: a) collecting or obtaining a biological sample (for example, a bodily fluid) from the subject; b) detecting or determining the presence (level) of semaphoring 3A in the biological sample; c) comparing the level of said semaphorin 3A to a control value; and d) determining the presence, stage, or efficacy of treatment of bladder cancer in the subject.

According to some embodiments, the methods of the invention may comprise one or more steps that may be performed in various orders.

For example, the method may be performed by the steps comprising:
 a) collecting or obtaining a biological sample ((for example, bodily fluid (e.g., a urine sample), tissue sample, and the like) from the subject;
 b) contacting the sample, under conditions such that a specific antigen-antibody complex may be formed, with antibodies directed to semaphorin 3A;
 c) determining or detecting the presence of semaphorin 3A-antibody complex formed, or quantifying the amount of sema3A-antibody complex formed; and
 d) comparing the level of sema3A in the biological sample to a control value.

According other embodiments, the method may be performed by the steps comprising:
 a) collecting a biological sample (e.g., a tissue sample) from the subject;

b) extracting RNA from the sample, inducing cDNA formation and amplifying semaphorin 3A cDNA using primers specific for semaphorin 3A;
c) determining the presence/quantity of semaphorin 3A cDNA formed; and
d) comparing the level of sema3A in the biological sample to a control value.

According to another aspect, the present invention provides a method for determining the effectiveness of a treatment of a subject with an anti-cancer treatment, comprising:
a) determining the levels of Semaphorin 3A in a first biological sample of said subject;
b) subjecting the subject with a treatment of cancer;
c) determining the levels of Semaphorin 3A in a second biological sample of said subject; and
d) comparing said levels of Semaphorin 3A in the first and second biological samples,
wherein a significant decrease in Semaphorin 3A levels from the first to the second biological samples is indicative of said treatment being efficacious.

According to some embodiments, one or more first samples are taken at a time point prior to initiation of the treatment for cancer and one or more second samples are taken at a time point during the treatment. According to some embodiments, one or more first samples are taken at a time point during the treatment (step b) and one or more second samples are taken at a time point during the treatment and subsequent to the time point of the one or more first samples. According to some embodiments, one or more first samples are taken at a time point during the treatment (step b) and one or more second samples are taken at a time point after the treatment has been discontinued. According to some embodiments, a decrease in the level of the semaphorin 3A exhibited in the at least one second sample as compared to that determined for the first sample is indicative that the treatment is effective. According to some embodiments, an increase in the level of semaphorin 3A in the at least one second samples as compared to the first sample is indicative that the treatment is ineffective (or unsuccessful).

As used herein the term "treatment of cancer" encompasses any treatment of cancer known in the art and includes, without limitation, surgery, drug therapy and radiation therapy. Exemplary drug therapies include, without limitation, chemotherapeutics, drug conjugates, immunotherapy and the alike. Each possibility represents a separate embodiment of the invention.

Surgical options to treat bladder cancer include, without limitation, transurethral bladder tumor resection (TURBT) (also used for diagnosis and staging), partial cystectomy (partial removal of the bladder), cystectomy (removal of the whole bladder and possibly nearby tissues and organs).

The type of chemotherapeutics used depends on the stage and grade of the tumor. Treatment with chemotherapeutics may be either intravesical (local) chemotherapy delivered into the bladder through a catheter that has been inserted through the urethra or systemic chemotherapy. Mitomycin and thiotepa are the drugs used most often for intravesical chemotherapy. Other drugs that are used include doxorubicin, gemcitabine, and valrubicin. For systemic chemotherapy a combination of four drugs, called MVAC, (methotrexate, vinblastine, doxorubicin, and cisplatin) is most often used. The combination of gemcitabine plus cisplatin is also used and has comparable anticancer effects to MVAC for patients with metastatic disease.

The standard immunotherapy drug for bladder cancer is a weakened bacterium called *bacillus* Calmette-Guerin (BCG), which is antigenically similar to a form of mycobacteria that causes tuberculosis. Interferons are another immunotherapy drugs that can be given as intravesical therapy. Interferons may be combined with BCG.

According to another aspect, the present invention provides a method for determining severity or prognosis of cancer in a subject, said method comprising:
a) determining the levels of a semaphorin 3A, or a derivative thereof, in a biological sample obtained from the subject; and
b) comparing the levels of the semaphorin 3A with the levels of at least one control value;
wherein an elevation in the levels of said semaphorin 3A compared to the levels of at least one control value is indicative of the severity of cancer or poor prognosis of said subject.

According to some embodiments, the method of "determining severity" of cancer refers to classifying the severity of the cancer of a subject according to a particular method of grading or staging.

According to some embodiments, the method of "determining severity" of cancer refers to determining cancer progression. In accordance with this embodiment, the control value is a value of the subject to which cancer progression is assessed. According to some embodiments, the method of "determining severity" of cancer refers to determining prognosis of the cancer.

According to some embodiments, the present methods are applicable for determining both primary as well as secondary cancers. According to some embodiments, the cancer is a primary cancer. According to other embodiments, the cancer is a secondary cancer, i.e., a metastatic cancer. According to some embodiments, the cancer has been recurred after complete or partial remission of the primary or metastatic tumor.

Thus, the methods disclosed herein are applicable for determining a cancer state, cancer severity as well as treatment efficiency at any stage of cancer as well as for determining recurrent cancer.

As used herein the term "Cancer recurrence" is interchangeable with "cancer relapse" and refers to the return of a sign, symptom or disease after a remission. The cancer cells may re-appear in the same site of the primary tumor or in another location, such as in secondary cancer.

The TNM (tumor size, lymph node involvement, and metastases formation) classification of malignant tumors is a cancer staging notation system that gives codes to describe the stage of a person's cancer, when this originates with a solid tumor.

The TNM system, classifies the tumor size and location ("T") as follows: carcinoma in situ (CIS)—very early, high grade, cancer cells are only in the innermost layer of the bladder lining; Ta—non-invasive papillary tumor; T1—invasive but not as far as the muscular bladder layer; T2—invasive into the muscular layer; T3—invasive beyond the muscle into the fat outside the bladder; T4—invasive into surrounding structures like the prostate, uterus or pelvic wall.

The term "invasive" as used herein refers to cells which have the ability to infiltrate surrounding tissue. The terms "non-invasive bladder cancer" or "non-invasive papillary tumor" as used herein refer to a very early cancer or a cancer that has not spread beyond the tissue of origin. According to particular embodiments, the non-invasive bladder cancer is selected from Ta or T1 stages. According to another embodiment, the non-invasive bladder cancer is at Ta stage. According to another embodiment, the non-invasive bladder cancer is at T1 stage.

The term "invasive cancer" refers to cancer that has spread beyond the layer of tissue in which it started into the normal surrounding tissues. Invasive cancers may or may not be metastatic. The term "muscle invasive bladder cancer" as used herein refers to a tumor that has spread into and/or beyond the muscular layer of the bladder. According to particular embodiments, the muscle invasive bladder cancer is selected from at least one stage selected from T2, T3 or T4 stages, as detailed hereinabove.

The TNM system, classifies involvement of lymph nodes ("N") as follows: NX—the regional lymph nodes cannot be evaluated; N0—the cancer has not spread to the regional lymph nodes; N1—the cancer has spread to a single regional lymph node in the pelvis; N2—the cancer has spread to more than one regional lymph node in the pelvis; and N3—the cancer has spread to the common iliac lymph nodes, which are located behind the major arteries in the pelvis, above the bladder.

The TNM system, classifies metastasis ("M") formation as follows: M0—the disease has not metastasized; and M1—there is distant metastasis.

By combining the "T", "N", and "M" categories the stage of the cancer is determined according to the following pTa (pathological) stages: Stage pTa—cancer cells are found only on the inner lining of the bladder, the renal pelvis or the ureter (mucosa). Stage pT1—cancer cells have proliferated to the layer beyond the inner lining of the urinary bladder (lamina propria), the renal pelvis or the ureter, but not to the muscles of the bladder, the renal pelvis or the ureter, respectively. Stage pT2: cancer cells have proliferated to the muscle layer in the bladder wall, the renal pelvis or the ureter, but not to the fatty tissue that surrounds the urinary bladder, the renal pelvis or the ureter, respectively. Stage pT3—cancer cells have proliferated to the fatty tissue surrounding the urinary bladder, the renal pelvis or the ureter. Stage pT4—cancer cells have proliferated to adjacent organs such as prostatic gland stroma, vagina, or uterus, but not to the lymph nodes or other organs. Stage pTxN1,M1—cancer cells have proliferated to the lymph nodes, pelvic or abdominal wall, and/or other organs. Recurrent: cancer has recurred in the urinary bladder, the renal pelvis or ureter or in another nearby organ after having been treated. According to a particular embodiment, the non-invasive bladder cancer is selected from stages: pTa and pT1.

According to some embodiments, the method of the invention is useful for determining at least one of the above mentioned "T", "N", and "M" categories. For example, semaphorin 3A levels of up to 7, or 8 ng/ml indicates that said cancer is at the stage of Ta. According to some embodiments, semaphorin 3A levels of at least 10 or 11 ng/ml indicates that the cancer is at the stages of T1 and above.

As used herein the term "grade" of the bladder cancer describes the degree of differentiation. Typically, bladder cancer is classified according to the following categories: a well-differentiated or low grade (hereinafter "LG"), and a poorly differentiated or high grade (hereinafter "HG"). According to some embodiments, the method of the invention is useful for determining the grade of the bladder cancer.

The methods of the invention are useful for "managing subject treatment" by the clinician or physician subsequent to the determination of treatment efficacy or severity of the cancerous state (e.g., cancer status). For example, if the severity of the cancerous state indicates that surgery is appropriate, the physician may schedule the patient for surgery. Alternatively, if the severity of the cancerous state is acute or a late stage cancer, no further action may be warranted. Furthermore, if the results show that treatment has been successful, no further management may be necessary. Alternatively, if the result of the methods of the present invention is inconclusive or there is reason that confirmation of status is necessary, the physician may order more tests.

According to some embodiments, the present invention provides a diagnostic method. Typically, diagnostic methods differ in their sensitivity and specificity. The "sensitivity" of a diagnostic assay is the percentage of diseased individuals who test positive (percent of "true positives"). Diseased individuals not detected by the assay are "false negatives". Subjects who are not diseased and who test negative in the assay are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

According to some embodiments, the method distinguishes a cancer state with a sensitivity of at least 60%, at least 70%, at least 80% or at least 90% when compared to normal subjects (e.g., a healthy individual not afflicted with cancer). Each possibility represents a separate embodiment of the invention. According to some embodiments, the method distinguishes a cancer state with a specificity of at least 60%, at least 70%, at least 80%, or at least 90% when compared to normal subjects (e.g., a healthy individual not afflicted with cancer). As used herein, sensitivity relates to the number of positive (diseased) samples detected out of the total number of positive samples present; specificity relates to the number of true negative (non-diseased) samples detected out of the total number of negative samples present.

As used herein the term "subject" is interchangeable with an individual or patient. According to some embodiments, the subject is a mammal According to some embodiments, the subject is a human According to some embodiments, the subject is symptomatic. According to other embodiments, the subject is asymptomatic. According to some embodiments, the subject is suspected of having a urothelial cancer (e.g. in the bladder). According to some embodiments, the subject is at risk for developing a urothelial cancer. Example of risk factors for developing bladder cancer include, but are not limited to, smoking, a parasite infection, radiation and chemical exposure.

Diagnostic Kits

According to another aspect, the present invention provide kits for the prognosis, diagnosis, monitoring urothelial cancer severity and/or determining efficacy of a treatment for cancer, comprising means for determining the levels of semaphorin3A, or a derivative thereof, in a biological sample of a subject and instructions for using said kits.

According to some embodiments, the "means for determining the levels of semaphorin3A" comprise a method by which levels of an mRNA, protein a peptide or a polypeptide of semaphorin 3A may be detected. According to some embodiments, the kit comprises means for detecting mRNA of semaphorin 3A. In accordance with this embodiment, the kit comprises primers specific for semaphorin 3A. According to some embodiments, the kit comprises means for detecting a peptide/polypeptide/protein of sema3A. In accordance with this embodiment, the kit comprises antibodies specific to semaphorin 3A. According to some embodiments, the kit comprises vessels for collecting the biological sample of a subject. According to some embodiments, the kit comprises a vessel suitable for collecting a fluid sample, such as a plastic bag or glass. According to some embodiments, the kit comprises a vessel suitable for storing a tissue sample. According to some embodiments, the vessel is a sterile vessel. According to some embodiments, the kit may further comprise negative and/or positive control samples. For example, control samples may contain a sample from at least one healthy individual (negative control) or at least one individual identified with a urothelial cancer (positive control), a panel of control samples from a set of healthy individuals or diseased individuals, or a stored set of data corresponding to control individuals. According to some embodiments, the kit may contain control samples obtained from patients having superficial or invasive tumors.

In various embodiments, the control value or control sample may be a negative control corresponding to a healthy subject, e.g. a value obtained from a healthy control individual not diagnosed with a disease, a panel of control values from a set of healthy individuals, and a stored set of data corresponding to control individuals that are not afflicted with a urothelial cancer, a positive control corresponding to a subject having low-grade urothelial cancer, e.g. a value obtained from an individual having non-invasive urothelial cancer, a panel of control values obtained from individuals having non-invasive urothelial cancer, and a stored set of data corresponding to control individuals, or a positive control corresponding to a subject having invasive urothelial cancer, e.g. a value obtained from an individual having invasive urothelial cancer, a panel of control values obtained from individuals having invasive urothelial cancer, and a stored set of data corresponding to control individuals having muscle-invasive cancer.

The following examples are presented in order to more fully illustrate some embodiments of the invention. They should, in no way be construed, however, as limiting the broad scope of the invention.

EXAMPLES

Example 1

Positive Correlation Between Semaphorin 3A Levels in the Urine and Bladder Carcinoma Detection, Size, and Grading A prospective blinded study which included 41 patients was conducted. Urine sample was taken from 41 patients scheduled for cystoscopy and bladder lesion resection. Corresponding samples were taken from 5 healthy volunteers. Semaphorin 3A levels was measured in each participant and adjusted to serum creatinine. The study was repeated using different commercially available kits producing essentially the same results with no statistical difference. Among the 41 patients, 31 were males, 10 females, and 30 patients (73%) had history of bladder cancer. Five patients had positive urine cytology prior to surgery. During

TABLE 1 characteristics of the patients included in the study.

| | |
|---|---|
| Age (Mean, range) | 70.5 (49-90) |
| Sex | |
| Male (%) | 31 (76) |
| Female (%) | 10 (24) |
| Previous Hx of TCC (%) | 30 (73) |
| Previous BCG Tx (%) | 15 (37%) |

TABLE 1-continued characteristics of the patients included in the study.

| | |
|---|---|
| Previous MMC Tx (%) | 12 (29%) |
| Positive cytology (%) | 5 (12) |

Abbreviations:
Hx—history;
Tx—treatment;
BCG—Bacillus Calmette-Guerin (an immune stimulation treatment of bladder cancer);
MMC—mitomycin C.

TABLE 2 the surgical parameters of the patients included in the study.

| Endoscopy findings | |
|---|---|
| Positive (%) | 30 (73) |
| Negative (%) | 11 (27) |
| # of lesion (Mean, range) | 2.5 (0-20) |
| Size of largest lesion (Mean, range) | 14 mm (0-100) |
| T stage* | |
| X | 1 |
| a | 19 |
| 1 | 4 |
| ≥2 | 4 |
| Grade | |
| LG | 19 |
| HG | 8 |
| UTUC | 4 |
| LTUC | 23 |

*1 patients with no malignancy indication. X—urothelial tumor with an undetermined stage.
Abbreviations:
LG—Low grade;
HG—high grade;
UTUC—upper tract urothelial carcinoma;
LTUC—low tract urothelial carcinoma.

TABLE 3 correlation between the clinical and pathological parameters and semaphorin 3A levels.

| Variable | Semaphorin levels | P value |
|---|---|---|
| Positive vs negative cysto | 7.6 vs 3.19 | 0.0033 |
| Size of lesion (>10 vs ≤10) | 11.08 vs 4.9 | 0.034 |
| Previous BCG Tx | 6.6 vs 6.06 | 0.79 |
| Previous MMC Tx | 7.25 vs 4.4 | 0.09 |
| Previous Hx of TCC | 6.46 vs 6.39 | 0.96 |
| Solitary vs multiple lesions | 8.4 vs 6.5 | 0.49 |
| Cytology (pos vs neg) | 7.56 vs 4.2 | 0.16 |
| T ≥ 1 vs Ta | 11.11 vs 6.85 | 0.17 |
| LG vs HG | 8.37 vs 7.5 | 0.78 |

Abbreviations:
Hx—history;
Tx—treatment;
BCG—Bacillus Calmette-Guerin (an immune stimulation treatment for bladder cancer);
MMC—mitomycin C;
TCC—transitional cell carcinoma;
LG—low grade;
HG—high grade.

Figure 1:
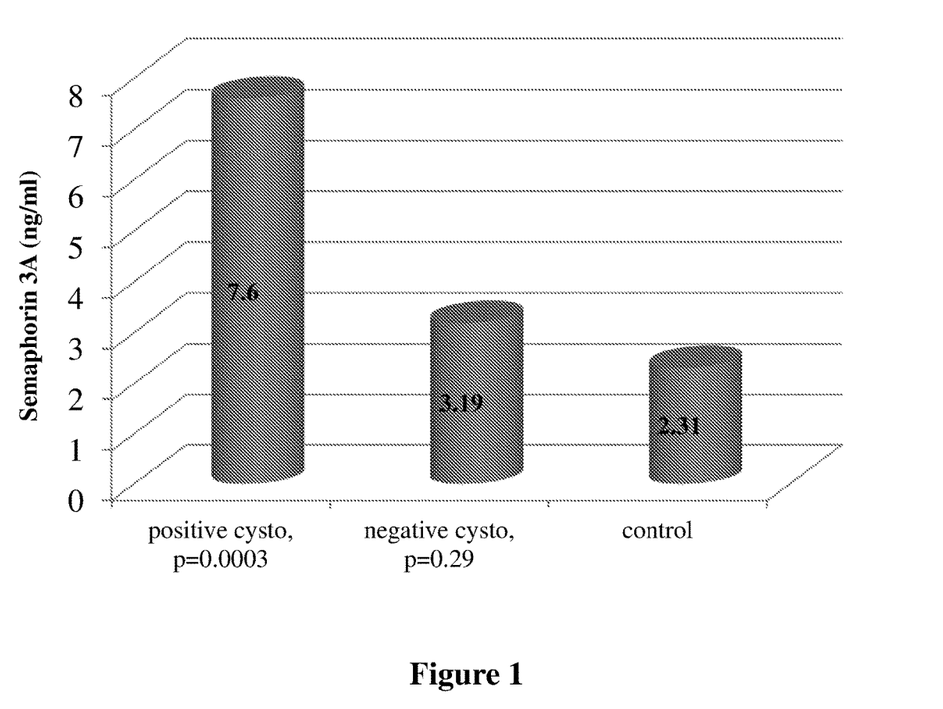
FIG. 1 is a bar graph demonstrating the levels of semaphorin 3A measured in the urine of patients with visualized tumors with later proven pathological biopsy of urothelial carcinoma (designated as positive cystoscopy), patients suspected of having bladder cancer in which no tumor was visualized in cystoscopy (designated as negative cystoscopy) and healthy subjects with no history of urothelial cancer and no urinary symptoms that did not undergo cystoscopy (control). Numbers which appear in the bars represent the average measurement of sema 3A in the urine samples.

As can be seen in FIG. 1, Semaphorin 3A levels were significantly higher in patients with tumors compared to patients without tumors and controls 7.6 (ng/ml) vs. 3.19 (ng/ml) and 2.31 (ng/ml) respectively (p=0.0003).

Figure 2:
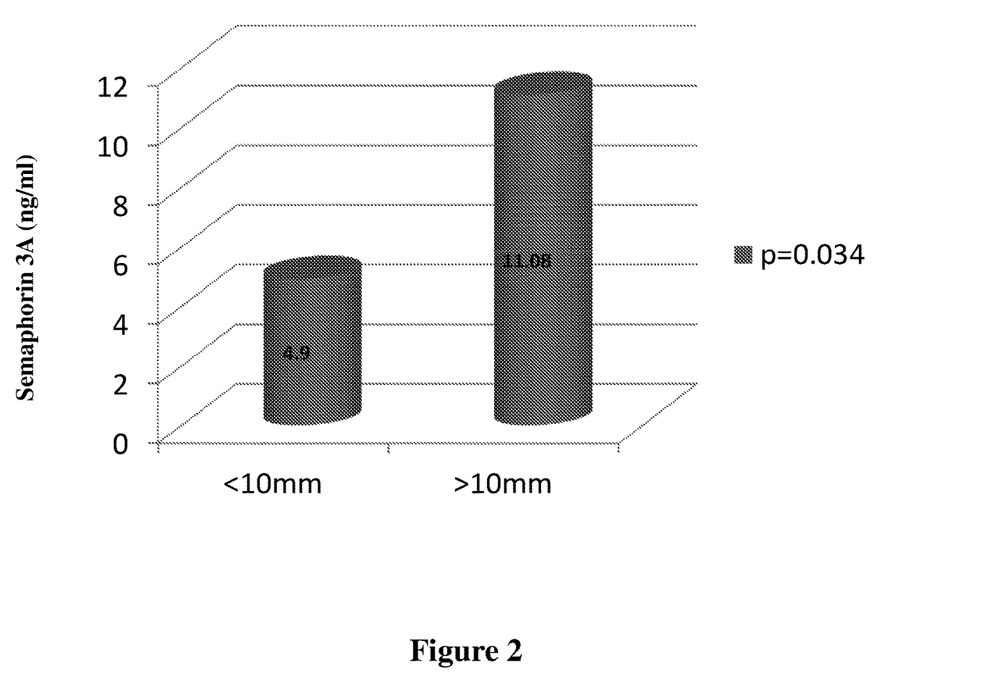
FIG. 2 is a bar graph demonstrating the levels of semaphorin 3A measured in the urine of patients with pathologically proven urothelial carcinoma having a size of below 10 mm or above 10 mm in the bladder. Numbers which appear in the bars represent the average measurement of sema 3A in the urine samples. This measurement represents tumors identified in the urethra, bladder, ureters, and intra renal collecting system.

As can be seen in FIG. 2, higher Semaphorin 3A levels positively correlate with tumor size, demonstrating that lesions largest than 10 mm had higher sema3A levels (11.8 vs. 4.9; p=0.034).

Figure 3:
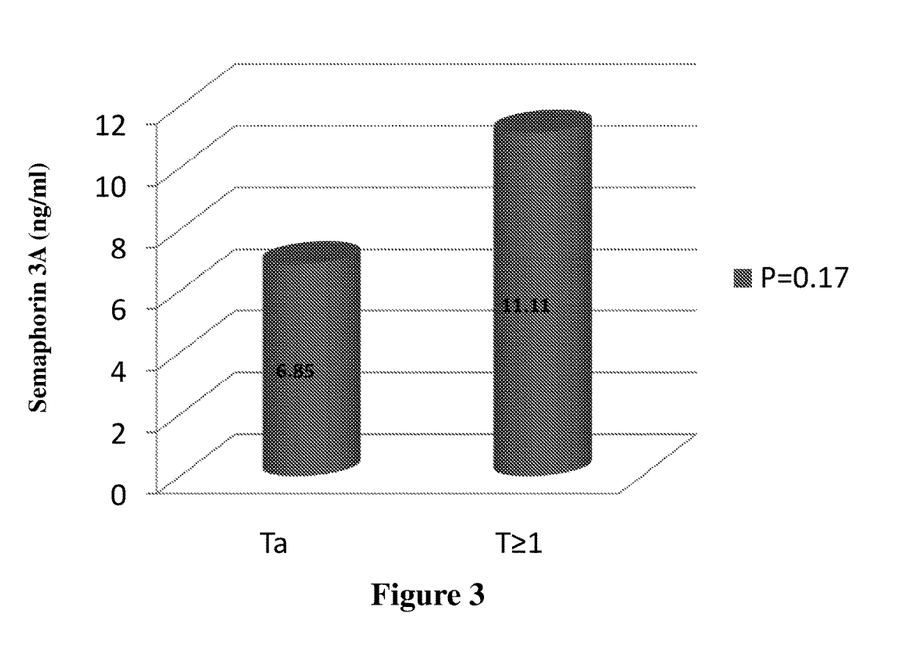
FIG. 3 is a bar graph demonstrating the levels of semaphorin 3A measured in the urine of patients with lesions in the bladder in which the lesions are classified into either Ta (tumor confined to the bladder mucosa) or T1 and above (tumor invades beyond the mucosa into the next layer the lamina propria and beyond). Numbers which appear in the bars represent the average measurement of sema 3A in the urine samples.
Figure 4:
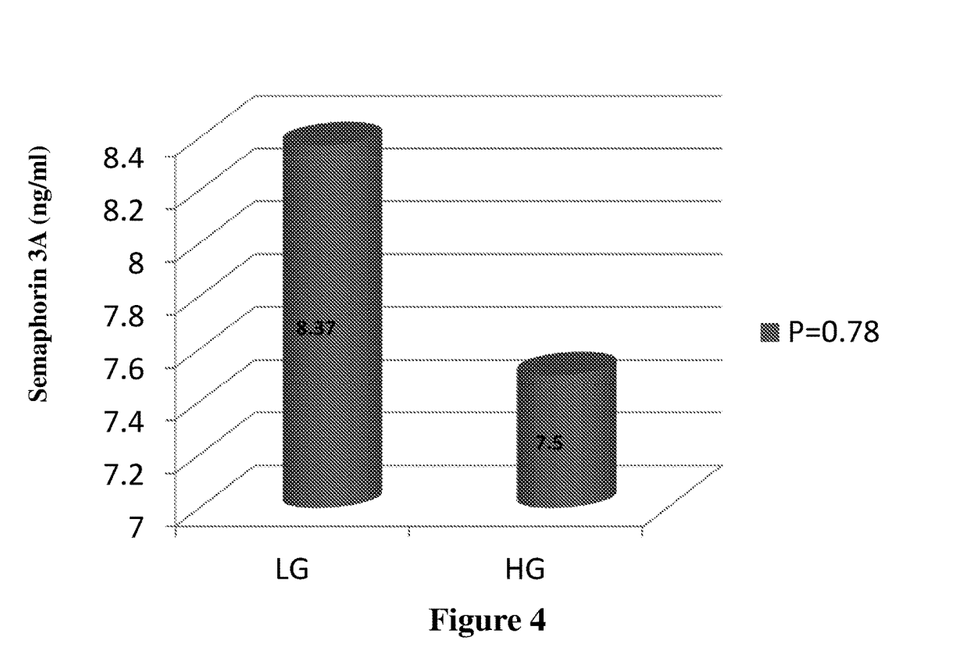
FIG. 4 is a bar graph demonstrating the levels of semaphorin 3A measured in the urine of patients with lesions in the bladder in which the lesions are classified into either well-differentiated (termed low grade; LG) cells or poorly differentiated (termed high grade; HG) cells. Numbers which appear in the bars represent the average measurement of sema 3A in the urine samples.

In addition, higher Semaphorin 3A levels positively correlated with tumor stage. Ta lesions had an average level of 6.85 (ng/ml) and T1 and above lesions had 11.11 (ng/ml) (see FIG. 3).

Figure 5:
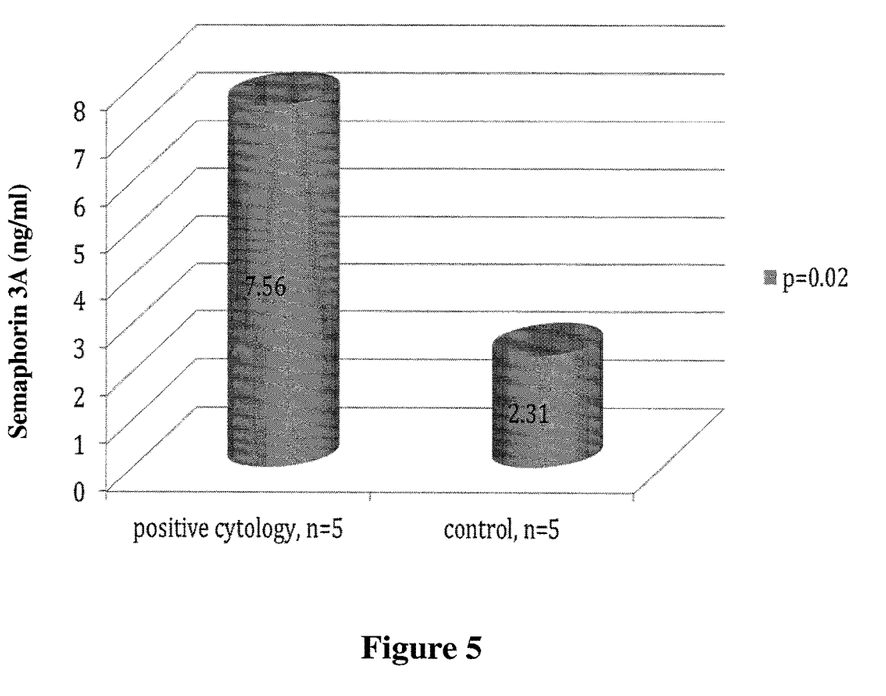
FIG. 5 is a bar graph demonstrating the levels of semaphorin 3A measured in the urine of patients with lesions in the bladder in which cytology indicated of existence of bladder carcinoma (positive) as compared to control patients with no tumor and negative cytology. Cytology is the traditional noninvasive method available today for bladder cancer detection. Numbers which appear in the bars represent the average measurement of sema 3A in the urine samples.

In compliance with urine cytology, high levels of Semaphorin 3A were detected in all cases with positive cytology with an average level of 7.56 (ng/ml). In control healthy subjects semaphorin 3A levels were 2.31 (ng/ml) in average (see FIG. 5).

Methods:

Urine samples were collected from patients suspected of TCC and from normal healthy controls. The samples were collected before the cystoscopy procedure. The samples were centrifuged at 2000 rpm for 15 minutes, in order to pellet the cells. The supernatant was collected and concentrated ×50 using centricone ("Milipore"). The concentrated urine samples were then subjected to human sema3A ELISA analysis according to the manufacturer instructions (MBS732622, MyBiosource).

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method for determining efficacy of a treatment for a urothelial cancer in a subject in need thereof, said method comprising:
    a) determining the levels of Semaphorin 3A in a first urine cytology sample of said subject;
    b) treating said subject with an anticancer treatment;
    c) determining the levels of Semaphorin 3A in a second urine cytology sample of said subject; and
    d) comparing the levels of Semaphorin 3A in said first and second urine cytology samples,
    wherein a decrease in Semaphorin 3A levels from the first to the second urine cytology sample is indicative of said treatment being efficacious.

2. The method of claim 1, wherein step a) is conducted at a time point prior to or during step b).

3. The method of claim 1, wherein steps a) and c) are conducted at distinct time points during step b).

4. The method of claim 1, wherein said cancer is an urothelial cancer of a tissue selected from the group consisting of: bladder, urethra, ureters, prostate, and renal pelvis.

5. The method of claim 4, wherein said urothelial cancer is bladder cancer.

6. The method of claim 5, wherein said bladder cancer is transitional cell carcinoma.

7. The method of claim 1, wherein said samples are free of residual cells.

8. The method of claim 1, further comprising concentrating said urine cytology samples.

9. The method of claim 1, wherein determining the levels of Semaphorin 3A comprises determining the protein levels of Semaphorin 3A.

10. The method of claim 1, wherein determining the levels of Semaphorin 3A comprises contacting the urine cytology samples with an antibody directed to Semaphorin 3A.

* * * * *